US009612245B2

(12) United States Patent
Rich et al.

(10) Patent No.: US 9,612,245 B2
(45) Date of Patent: Apr. 4, 2017

(54) MULTIPLE-PULSE PUMPING FOR ENHANCED FLUORESCENCE DETECTION AND MOLECULAR IMAGING IN CELLS AND TISSUE

(71) Applicants: University of North Texas Health Science Center, Fort Worth, TX (US); Texas Christian University, Fort Worth, TX (US)

(72) Inventors: Ryan M. Rich, Hurst, TX (US); Ignacy Gryczynski, Fort Worth, TX (US); Julian Borejdo, Dallas, TX (US); Zygmunt Gryczynski, Fort Worth, TX (US)

(73) Assignees: University of North Texas Health Science Center at Fort Worth, Fort Worth, TX (US); Texas Christian University, Fort Worth, TX (US)

( * ) Notice: Subject to any disclaimer, the term of this patent is extended or adjusted under 35 U.S.C. 154(b) by 0 days.

(21) Appl. No.: 14/322,998

(22) Filed: Jul. 3, 2014

(65) Prior Publication Data
US 2015/0011406 A1   Jan. 8, 2015

Related U.S. Application Data

(60) Provisional application No. 61/842,726, filed on Jul. 3, 2013.

(51) Int. Cl.
*G01N 21/64* (2006.01)
*G01N 33/58* (2006.01)

(52) U.S. Cl.
CPC ....... *G01N 33/582* (2013.01); *G01N 21/6428* (2013.01); *G01N 2201/0697* (2013.01)

(58) Field of Classification Search
CPC .............................. G01N 21/64; G01N 33/58
See application file for complete search history.

(56) References Cited

U.S. PATENT DOCUMENTS

| 6,159,686 A * | 12/2000 | Kardos et al. ............... 435/6.14 |
| 2006/0063264 A1* | 3/2006 | Turner ................... B01L 3/5085 |
| | | 436/8 |
| 2011/0220816 A1* | 9/2011 | Kakizaki ................ H05G 2/003 |
| | | 250/504 R |

OTHER PUBLICATIONS

Beams, R., et al., "Using a Single Diamond NV Center for Nanoscale Fluorescence Lifetime Imaging," in: Rochester Conf. Coherence Quantum Opt. Quantum Inf. Meas. Meet., Optical Society of America, 2013: p. M6.55.

(Continued)

*Primary Examiner* — David Porta
*Assistant Examiner* — Faye Boosalis
(74) *Attorney, Agent, or Firm* — Edwin S. Flores; Chalker Flores, LLP

(57) ABSTRACT

The present invention includes a method and system for enhancing the signal-to-noise ratio in emission detection comprising: selecting a probe capable of at least one of fluorescence, phosphorescence, or delayed fluorescence in or about a sample that comprises interfering background signal; and exposing the probe to one or more controllable bursts, each burst comprising two or more pulses, wherein the one or more controllable bursts of high repetition energy pulses enhance the signal from the probe above that of the background signal.

47 Claims, 10 Drawing Sheets

(56) References Cited

OTHER PUBLICATIONS

Becker, W., "Fluorescence lifetime imaging—techniques and applications," J. Microsc. 247 (2012) 119-136.
Bilan, D.S., et al., "HyPer-3: A Genetically Encoded H2O2 Probe with Improved Performance for Ratiometric and Fluorescence Lifetime Imaging," Acs Chem. Biol. 8 (2013) 535-542.
Clancy, B., "Reduction of background autofluorescence in brain sections following immersion in sodium borohydride," J. Neurosci. Methods. 83 (1998) 97-102.
Cowen, T., et al, "Pontamine sky blue: A counterstain for background autofluorescence in fluorescence and immunofluorescence histochemistry," Histochemistry. 82 (1985) 205-208.
Croce, A.C., et al, "Dependence of Fibroblast Autofluorescence Properties on Normal and Transformed Conditions, Role of the Metabolic Activity," Photochem. Photobiol. 69 (1999) 364-374.
Eliseeva, S.V., "Lanthanide luminescence for functional materials and bio-sciences," Chem. Soc. Rev. 39 (2009) 189-227.
Fore, S., et al., "Pulsed-Interleaved Excitation FRET Measurements on Single Duplex DNA Molecules Inside C-Shaped Nanoapertures," Nano Lett. 7 (2007) 1749-1756.
Funovics, M., et al., "Protease sensors for bioimaging," Anal. Bioanal. Chem. 377 (2003) 956-963.
Ghisla, S., et al., "Fluorescence and optical characteristics of reduced flavines and flavoproteins," Biochemistry (Mosc.). 13 (1974) 589-597.
Haralampus-Grynaviski, N.M., et al., "Spectroscopic and morphological studies of human retinal lipofuscin granules," Proc. Natl. Acad. Sci. 100 (2003) 3179-3184.
Jin, D., et al., "Time-Gated Luminescence Microscopy Allowing Direct Visual Inspection of Lanthanide-Stained Microorganisms in Background-Free Condition," Anal. Chem. 83 (2011) 2294-2300.
Lakowicz, J. R., et al., Fluorescence lifetime imaging, Anal. Biochem. 202 (1992) 316-330.
Leblond, R., et al., "Pre-clinical whole-body fluorescence imaging: Review of instruments, methods and applications," J. Photochem. Photobiol. B. 98 (2010) 77-94.
Muller, B.K., et al., "Pulsed Interleaved Excitation," Biophys. J. 89 (2005) 3508-3522.
Pepperkok, R., et al., "Simultaneous detection of multiple green fluorescent proteins in live cells by fluorescence lifetime imaging microscopy," Curr. Biol. 9 (1999) 269-274.
Rich, R., et al., "Properties of coatings on RFID p-Chips that support plasmonic fluorescence enhancement in bioassays", Anal. Bioanal. Chem. 404 (2012) 2223-2231.
Rich, R., et al., "Elimination of autofluorescence in fluorescence correlation spectroscopy using the AzaDiOxaTriAngulenium (ADOTA) fluorophore in combination with time-correlated single-photon counting (TCSPC)," Anal. Bioanal. Chem. 405 (2013) 4887-4894.
Rich, R., et al., "Elimination of autofluorescence background from fluorescence tissue images by use of time-gated detection and the AzaDiOxaTriAngulenium (ADOTA) fluorophore," Anal. Bioanal. Chem. 405 (2013) 2065-2075.
Rüttinger, S., et al., "Accurate single-pair Förster resonant energy transfer through combination of pulsed interleaved excitation, time correlated single-photon counting, and fluorescence correlation spectroscopy," J. Biomed. Opt. 11 (2006) 024012-024012.
Sánchez-Mosteiro, G., et al., "DNA-Based Molecular Wires: Multiple Emission Pathways of Individual Constructs," J. Phys. Chem. B. 110 (2006) 26349-26353.
Schneckenburger, H., et al., "Autofluorescence Lifetime Imaging of Cultivated Cells Using a UV Picosecond Laser Diode," J. Fluoresc. 14 (2004) 649-654.
Schnell, S.A., et al., "Reduction of Lipofuscin-like Autofluorescence in Fluorescently Labeled Tissue," J. Histochem. Cytochem. 47 (1999) 719-730.
Schweitzer, D., et al., "Time-Resolved Autofluorescence Imaging of Human Donor Retina Tissue from Donors with Significant Extramacular Drusen," Invest. Ophthalmol. Vis. Sci. 53 (2012) 3376-3386.
Tsien, R., "Building and breeding molecules to spy on cells and tumors," Febs Lett. 579 (2005) 927-932.
Yang, M., et al., "Whole-body optical imaging of green fluorescent protein-expressing tumors and metastases," Proc. Natl. Acad. Sci. 97 (2000) 1206-1211.
Yang, M., et al., "Visualizing gene expression by whole-body fluorescence imaging," Proc. Natl. Acad. Sci. 97 (2000) 12278-12282.

* cited by examiner

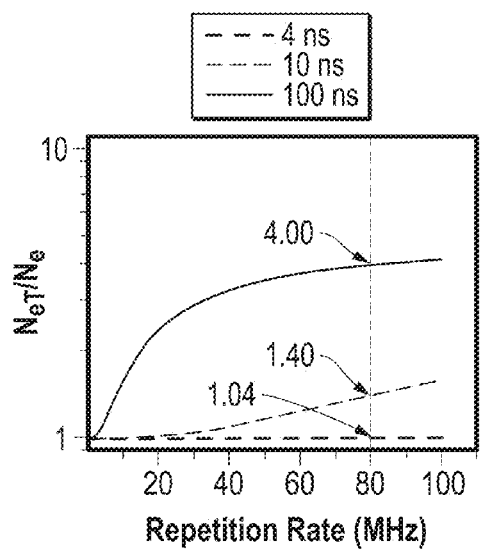
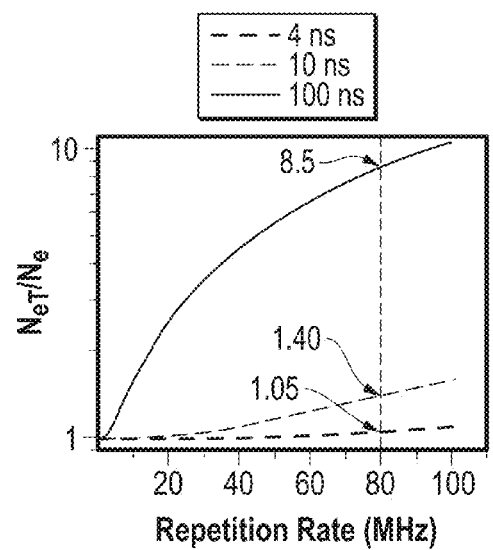
FIG. 1A
FIG. 1B
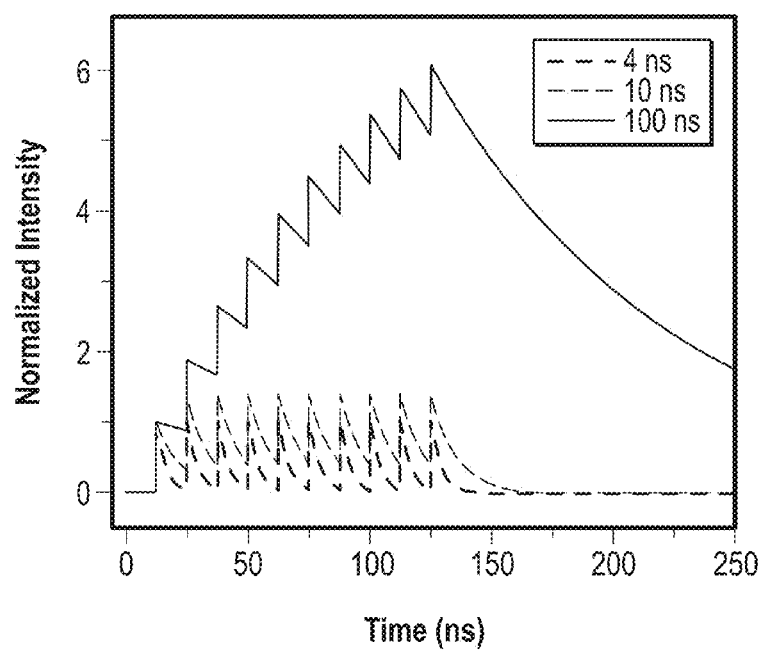
FIG. 2

MULTIPLE-PULSE PUMPING FOR ENHANCED FLUORESCENCE DETECTION AND MOLECULAR IMAGING IN CELLS AND TISSUE

STATEMENT OF FEDERALLY FUNDED RESEARCH

This invention was made with U.S. Government support by the NIH grant number NIH R01 EB012003. The government has certain rights in this invention.

CROSS-REFERENCE TO RELATED APPLICATIONS

This patent application is a non-provisional patent application of U.S. provisional patent application 61/842,726 filed on Jul. 3, 2013, which is hereby incorporated by reference in their entirety.

TECHNICAL FIELD OF THE INVENTION

The present invention relates in general to the field of emission/fluorescence detection, and more particularly, to the use of multiple-pulse pumping for enhanced fluorescence detection and molecular imaging in cells, tissue, organs, and body.

INCORPORATION-BY-REFERENCE OF MATERIALS FILED ON COMPACT DISC

None.

BACKGROUND OF THE INVENTION

Without limiting the scope of the invention, its background is described in connection with fluorescence detection.

Without limiting the scope of the invention, its background is described in connection with fluorescence spectroscopy and fluorescence microscopy. Fluorescence is a phenomenon that has provided many useful applications and fluorescence spectroscopy is a rapidly developing and crucial component in the areas of flow cytometry, medical diagnostics, DNA sequencing, genetics and cellular and molecular imaging, and tissue and organ imaging.

During the last couple of decades, fluorescence based imaging has made incredible progress, becoming one of the most versatile and widely utilized visualization techniques in research and biomedical diagnostics. The quickly increasing availability of new dyes and fluorescent proteins as well as technological progress opens new ways for noninvasive studies of fundamental processes from gene expression, protein function, and protein-protein interactions to cellular and tissue processes [1,2]. In addition to outstanding successes in microscopy, fluorescence based imaging is gaining momentum as an imaging method for whole-body, in-vivo investigation of molecular processes in small animals [3-5]. The development of bright probes and highly sensitive detectors puts fluorescence among most sensitive detections frequently allowing study of nanomolar and picomolar concentrations [6].

A fundamental limitation for cellular and tissue imaging is sample autofluorescence, which is the fluorescence of, e.g., endogenous components of cells, tissue, and fixatives. The large variety of autofluorescence sources produces a broad emission that overlaps with the emission of typical fluorescent dyes used for labeling [7-9]. Typically the brightness of such natural components is relatively low, but the overwhelming abundance of them results in a significant contribution to the observed fluorescence signal, especially in tissue samples. It is very difficult to reduce the signal from autofluorescence without altering the probe and/or the biological system [10-12], thus one typically increases the concentration of the dye to a level at which the fluorescence of the dye dominates the overall signal. Such a large increase in dye concentration is not always possible for various physiological reasons, and in many cases it may interfere with the biological process one wants to investigate. In cases where background is a problem, an increase in excitation intensity is not an option, since it always leads to a proportional increase in both background intensity and signal intensity. Despite recent advances, a need remains for overcoming sample autofluorescence.

SUMMARY OF THE INVENTION

The present invention includes in one embodiment a method for enhancing the signal-to-noise ratio in emission comprising: selecting a probe capable of at least one of fluorescence, phosphorescence, or delayed fluorescence in or about a sample that comprises interfering background signal; and exposing the probe and sample to one or more controllable bursts, each burst comprising two or more pulses, wherein the one or more controllable bursts of high repetition energy pulses enhance the signal from the probe above that of the background signal. In one aspect, the probe is selected from the group of long-lived emitters like ADOTA group of dyes, pyrene and dansyl type emitters, porphyrins based dyes, lanthanides probes, metal-ligand probes like ruthenium probes, quantum dots, or quantum nanomaterials, nanodiamonds; also probes 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9,10-bis(phenylethynyl) anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone; and Yellow fluorescent protein. In another aspect, the probe is exposed to 2, 3, 4, 5, 6, 7, 8, 9, 10, 11, 12, 13, 14, 15, 20, 25, 30, 35, 40, 45, 50, 100, 200, 300, 400, 500, 750, 1,000, $10^5$, $10^6$, $10^7$ or more burst trains before, during or prior to detection. In another aspect, each of the one or more bursts comprises 2, 3, 4, 5, 6, 7, 8, 9, 10, 11, 12, 13, 14, 15, 20, 25, 30, 35, 40, 45, 50 100, 200, 300, 400, 500, 750, 1,000 pulses before, during or prior to detection. In another aspect, the frequency in bursts is higher than the repetition of the burst. In another aspect, each of the bursts, the pulses, or both are of a different wavelength. In another aspect, the number of pulses in a burst is variable. In another aspect, the pulses are spaced as one or more low repetition packets. In another aspect, the time between bursts is timed to optimize the detection of the probe. In another aspect, the time between bursts is larger than the time between pulses in each burst.

In one aspect, the method further comprises the step of detecting the signal from the probe. In another aspect, the method further comprises the step of detecting the signal from the probe and wherein detection of the signal from the probe is as least one of a time-gated or time-delayed detection. In another aspect, the pulses have a controllable bursts comprise a range from 1 kHz up to the repetition rate of the pulses in a burst. In another aspect, the pulse duration can be from femtoseconds (Ti:Sapphire type lasers), picosecond (laser diodes, dye lasers, and Sapphire lasers), nanoseconds (Nitrogen or Argon lasers), pulsed laser diodes and light emitting diodes (with pulse duration from picosecond to milliseconds). In another aspect, the background signal is from at least one of a cell, a tissue, a cellular sample or tissue sample on a slide, an organ or whole animal, a human organ, tissue, or whole body imaging. In another aspect, the background signal is from at least one of a diagnostic test, a solvent, a DNA array, a RNA array, a gel, paper, a cellulose, or any supporting matrix. In another aspect, wherein the background signal has a shorter lifetime that the probe. In another aspect, the method further comprises the step of imaging the fluorescence, phosphorescence, or delayed fluorescence from the sample. In another aspect, the method further comprises the step of imaging the fluorescence, phosphorescence, or delayed fluorescence from a virus, bacterial, fungi, plant, animal, or human.

Another embodiment of the present invention includes an apparatus for enhancing the signal-to-noise ratio from an emission comprising: a source of electromagnetic radiation capable of exciting a probe selected from at least one of fluorescence, phosphorescence, or delayed fluorescence, in or about a sample having an interfering background signal, wherein the source is capable of delivering one or more controllable bursts, each of the bursts comprising two or more pulses, wherein the one or more controllable bursts of pulses contact and excite the probe in or about the sample to enhance the signal from the probe above that of the background signal. In one aspect, the probe is selected from the group of long-lived emitters like ADOTA group of dyes, pyrene and dansyl type emitters, porphyrins based dyes, lanthanides probes, metal-ligand complexes like ruthenium probes, quantum dots, or quantum nanomaterials, nanodiamonds; also probes 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone; and Yellow fluorescent protein. In another aspect, the probe is exposed to 2, 3, 4, 5, 6, 7, 8, 9, 10, 11, 12, 13, 14, 15, 20, 25, 30, 35, 40, 45, 50, 100, 200, 300, 400, 500, 750, 1,000, $10^5$, $10^6$, $10^7$ or more burst trains before, during or prior to detection. In another aspect, each of the one or more bursts comprises 2, 3, 4, 5, 6, 7, 8, 9, 10, 11, 12, 13, 14, 15, 20, 25, 30, 35, 40, 45, 50, 100, 200, 300, 400, 500, 750, 1,000 pulses before, during or prior to detection. In another aspect, the frequency in bursts is higher than the repetition of the burst. In another aspect, each of the bursts, the pulses, or both are of a different wavelength. In another aspect, the number of pulses in a burst is variable. In another aspect, the pulses are spaced as one or more low repetition packets. In another aspect, the time between bursts is timed to optimize the detection of the probe. In another aspect, the time between bursts is larger that the time between pulses in each burst.

In one aspect, the apparatus further comprises the step of detecting the signal from the probe. In another aspect, the apparatus further comprises the step of detecting the signal from the probe and wherein detection of the signal from the probe is as least one of a time-gated or time-delayed detection. In another aspect, the pulses have a controllable bursts comprise a range from 1 kHz up to the repetition rate of the pulses in a burst. In another aspect, the pulse duration can be from femtoseconds (Ti:Sapphire type lasers), picosecond (laser diodes, dye lasers, and Sapphire lasers), nanoseconds (Nitrogen or Argon lasers), pulsed laser diodes and light emitting diodes (with pulse duration from picosecond to milliseconds). In another aspect, the background signal is from at least one of a cell, a tissue, a cellular sample or tissue sample on a slide, an organ or whole animal, a human organ, tissue, or whole body imaging. In another aspect, the background signal is from at least one of a diagnostic test, a solvent, a DNA array, a RNA array, a gel, paper, a cellulose, or any supporting matrix. In another aspect, the background signal has a shorter lifetime that the probe. In another aspect, the apparatus further comprises the step of imaging the fluorescence, phosphorescence, or delayed fluorescence from the sample. In another aspect, the apparatus further comprises the step of imaging the fluorescence, phosphorescence, or delayed fluorescence from a virus, bacterial, fungi, plant, animal, or human. In another aspect, the apparatus further comprises a microscope for imaging the fluorescence, phosphorescence, or delayed fluorescence from the sample. In another aspect, the apparatus further comprises an apparatus for imaging the fluorescence, phosphorescence, or delayed fluorescence from a virus, bacterial, fungi, plant, animal, or human.

Yet another embodiment of the present invention includes a kit for retrofitting an apparatus to produce one or more burst of electromagnetic pulses, each of the bursts comprising two or more pulses comprising: a burst generator that creates a burst of two or more pulses of electromagnetic radiation from a source pulse by separating the source pulse into two or more pulses to form a burst of pulses, wherein the spacing between each burst of pulses, and the frequency of the pulses, is selected to match the excitation of one or more probes. In one aspect, the burst generator comprises at least one of mirrors, prisms, gratings, splitters, optoelectronic elements, mechanical elements, optic fiber, or optic fiber loops. In another aspect, the kit further comprises an attachment for a microscope to the one or more bursts of pulses in communication with a target. In another aspect, the probe is selected from the group of long-lived emitters like ADOTA group of dyes, pyrene and dansyl type emitters, porphyrins based dyes, lanthanides probes, metal-ligand complexes like ruthenium probes, quantum dots, or quantum nanomaterials, nanodiamonds; also probes 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CFSE; Calcein; Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide;

Pyranine; Rhodamine; RiboGreen; Rubrene; Ruthenium(II) tris(bathophenanthroline disulfonate); SYBR Green; Stilbene; TSQ; Texas Red; Umbelliferone; and Yellow fluorescent protein. In another aspect, the burst generator generates one or more bursts of pulses that exposed the probe to 2, 3, 4, 5, 6, 7, 8, 9, 10, 11, 12, 13, 14, 15, 20, 25, 30, 35, 40, 45, 50, 100, 200, 300, 400, 500, 750, 1,000, $10^5$, $10^6$, $10^7$ or more burst trains before, during or prior to detection. In another aspect, the burst generator generates one or more bursts that comprises 2, 3, 4, 5, 6, 7, 8, 9, 10, 11, 12, 13, 14, 15, 20, 25, 30, 35, 40, 45, 50, 100, 200, 300, 400, 500, 750, 1,000 pulses before, during or prior to detection. In another aspect, the kit further comprises a light source capable of transmitting the source pulse.

BRIEF DESCRIPTION OF THE DRAWINGS

For a more complete understanding of the features and advantages of the present invention, reference is now made to the detailed description of the invention along with the accompanying figures and in which:

FIGS. 1a and 1b are graphs that show molecules in the excited state as a function of repetition rate (RR). The number of molecules in the excited state at the instant that an excitation pulse arrives is calculated using FIG. 1a: Equation (2) for five pulses (n=5), and FIG. 1b: Equations (1) and (3) for infinite pulses. The solid line represents calculations for a fluorophore with a 100 ns lifetime, the dashed line for 10 ns, and the heavy dashed line for 4 ns, the last of which being the approximate lifetime for commonly-used organic dyes. Increasing the RR increases the excited state population at a rate which increases fro longer-lived dyes. Note that the vertical axes are logarithmic. The dotted, vertical line is drawn at RR=80 MHz, a commonly available RR for pulsed diode lasers.

FIG. 2 is a graph that shows a model of fluorescence decay from bursts of 10 excitation pulses. The heavy dashed line shows the calculated decay curve for a fluorophore with a 4 ns lifetime, the dashed line for 10 ns, and the solid line for 100 ns. The repetition rate for the pulses within the burst was 80 MHz, or 12.5 ns between pulses.

FIGS. 7a through 7d depict a bead loaded with the long-lived Ru on a background of short-lived SRB, and the intensity scales are normalized to the full intensity span of FIG. 7d. The image in FIG. 7a shows the result of 1-pulse excitation, FIG. 7b shows 2-pulse excitation, FIG. 7c shows 5-pulse excitation, and FIG. 7d shows 10-pulse excitation. The image in FIG. 7e depicts 1-pulse excitation, but the average laser power has been increased to the average laser power of the pulse train involving 10-pulse bursts in FIG. 7d. The Signal to background ratio in FIG. 7e differs by 3% from that of FIG. 7a. Each surface plot, FIGS. 7f through 7j, corresponds to the image, FIGS. 7a through 7e above it. The boxes in images 7a through 7d indicate the area from which the data in FIGS. 8a and 8b were collected.

FIG. 8b shows each of the decay curves, a two-component exponential decay fitting was performed with the lifetimes of the two components fixed at 1.65 ns (SRB background) and 375 ns (bead labeled with Ru). The amplitude of the long-lived component is shown as the percentage of the overall amplitude in the pane on the right. The clear square in FIG. 8b shows percentage computed for the high intensity, 1-pulse excitation depicted in FIG. 7d, whose decay is not shown in 8a in order to increase clarity.

DETAILED DESCRIPTION OF THE INVENTION

Figure 3:
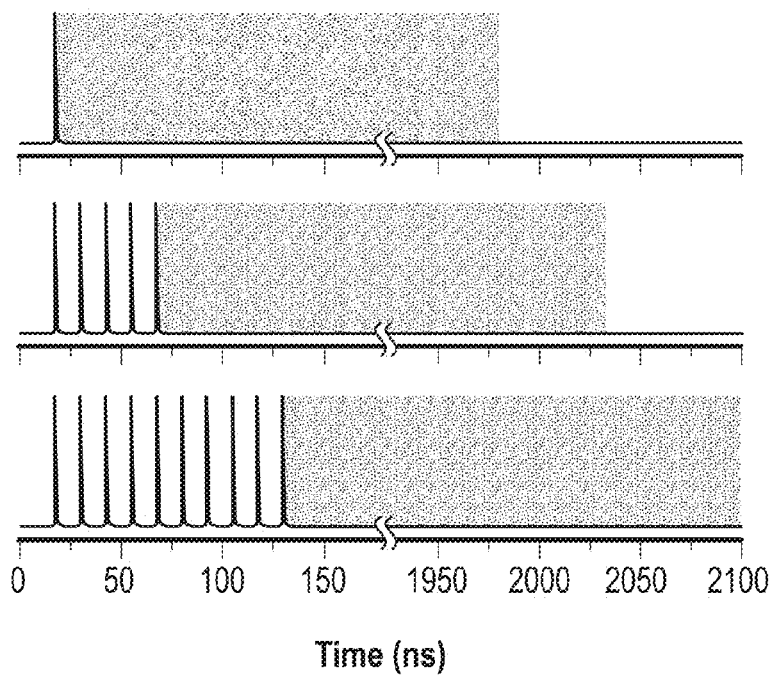
FIG. 3 shows three schematics of multiple pulse excitation schemes. The t=0 point is the time at which the synchronization pulse reached the TCSPC module. The shaded box shows the window from which photons were collected. This window remained the same for all multiple pulse excitation schemes. Note that the time scale is broken here, as a relative large amount of time was provided to allow all fluorophores to decay completely.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present inventors recognized that autofluorescence is characterized by complex fluorescence intensity decay with multiple fluorescent lifetimes ranging from subnanoseconds to a few nanoseconds, but typically not exceeding 6-7 ns [13-15]. The development of long-lived fluorophores with fluorescence lifetimes longer than 10 ns and the use of so-called time-gated detection dramatically increase the signal to background ratio in microscopy and tissue imaging. While time-gated detection reduces the overall signal, it reduces the signal of the short-lived background to a greater extent than the long-lived probe. However, the signal from a moderately long-lived probe (~10-20 ns lifetime) will still be adversely impacted [16]. Extremely long-lived probes like those based on lanthanide atoms [17] have been shown to allow detection at practically background free conditions [18], but unfortunately the fundamental physics/chemistry dictates that such long-lived probes typically have low extinction coefficients and relatively low quantum yields, leading to a low overall brightness of the probe.

In spite of many difficulties, fluorescence lifetime imaging (FLIM) has been very successful and lead to many practical applications [19-23]. Further, the development of the pulsed lasers and lasers diodes that are now widely available with many typical imaging systems opens many new applications for FLIM. Advanced electronics and computers now allow for very precise control of the pulse repetition rate and pulse sequences for single or even multiple laser diodes. Very successful applications of Forster resonance energy transfer (FRET) in microscopy recently stimulated development of the pulse interleave excitation (PIE) approach using interleaved pulses of two colors that allows for independent control of donor and acceptor emissions [24-27]. The present inventors have developed a new method that uses controllable bursts of single color pulses to significantly increase the fluorescence signal of a long-lived marker over the endogenous fluorescent background and scattering. The invention includes a simple method that uses well-separated bursts of closely spaced excitation pulses, while the signal collection for time correlated single photon counting (TCSPC) is synchronized with the last pulse in the burst. Systems capable of realizing such sequences of pulses are readily available from commercial producers like Picoquant Inc., Horiba Inc., or Becker & Hickel. Briefly, a "pumping" a long-lived fluorescent dye to an excited state with a series (burst) of ps, high repetition (closely spaced) laser pulses, while the short-lived background stays constant from pulse-to-pulse. The inventors demonstrate herein that the extent of this pumping is dependent upon the lifetime of the probe and the repetition rate within the excitation burst, and show that when applied to a fluorescence probe with a lifetime of 10 ns or longer, the pumping by commercially available, high repetition rate (80 MHz-100 MHz) laser diodes can significantly increase the signal-to-background ratio, easily exceeding an order of magnitude, including using a confocal microscope. This new approach opens new ways for highly enhanced imaging capabilities using existing technology and without sacrificing the probe signal or photostability.

Applications of fluorescence based imaging techniques for detection in cellular and tissue environments are severely limited by autofluorescence of endogenous components of cells, tissue, and the fixatives used in sample processing. To achieve sufficient signal-to-background ratio, a high concentration of the probe needs to be used which is not always feasible. Since typically autofluorescence is in the nanosecond range, long-lived fluorescence probes in combination with time-gated detection can be used for suppression of unwanted autofluorescence. Unfortunately, this requires the sacrifice of the large portion the probe signal in order to sufficiently filter the background.

The present invention includes a simple and practical approach to achieve a many-fold increase in the intensity of a long-lived probe without increasing the background fluorescence. Using controllable, well-separated bursts of closely spaced laser excitation pulses, the inventors are able to highly increase the fluorescence signal of a long-lived marker over the endogenous fluorescent background and scattering, thereby greatly increasing detection sensitivity. Using a commercially available confocal microscopy system equipped with a laser diode and time correlated single photon counting (TCSPC) detection, the inventors are able to enhance the signal of a long-lived Ruthenium-based probe by nearly an order of magnitude. The inventors used 80 MHz bursts of pulses (12.5 ns pulse separation) repeated with a 320 kHz repetition rate as needed to adequately image a dye with a 380 ns lifetime. Just using 10 pulses in the burst increases the Ru signal almost 10 fold without any increase in the background signal.

The large majority of studies involving fluorescent dyes are conducted under the condition where only a very small number of the fluorescent molecules are excited. Many time-resolved microscopy systems use picosecond pulsed diode lasers with typical average intensity in the range of a few mW for excitation and time-correlated single photon counting (TCSPC) detection. In fact, less than 500 μW actually reaches the sample, depending on the microscope's optics, thus, only a small fraction of the molecules in the typical confocal volume (<1 fl) can be excited by a single, picosecond pulse. Since such confocal volume would contain well over 1000 molecules of a dye that has a micromolar concentration, the small fraction of excited molecules can still provide sufficient photon flux, provided that the laser repetition rate is in the kHz-MHz range. However, as already explained, the detected signal is typically a sum of photons emitted by dye molecules as well as endogenous chromophores from the sample that constitute sample background.

The repetition rate (RR) used in TCSPC systems is usually determined by the fluorescence lifetime of the dye. To avoid problems in data analysis, the time between pulses (1/RR) may be 5-10 longer than the fluorescence lifetime of longest lifetime component of the sample, but can be increased or decreased depending on, e.g., the fluorescent probes selected, the nature of the autofluorescence, time, temperature, use of additional probes, type of sample being imaged. Otherwise the fluorescence decay of a particular pulse would overlap with that of the subsequent pulse. Hence, for typical dyes like fluorescein with fluorescence lifetimes of 4 ns or less, a RR of less than 20-40 MHz is acceptable. When fluorophores with longer lifetimes are used, typically one decreases the RR to allow the excited state to completely decay before subsequent pulses arrive.

Here the inventors consider the case when the RR is not sufficiently low to allow the complete decay after each excitation pulse. If the number of fluorophores in the excitation volume is $N_0$ and a single pulse excites $N_e$ molecules, then the observed fluorescence intensity will be proportional to the number of molecules excited by each pulse ($I \sim N_e$). This situation changes when the RR approaches the level such that subsequent pulses arrive before the excited population can decay completely. For simplicity, assuming that $N_0 \gg N_e$, and assuming that depletion of the ground state is negligible and each pulse excites $N_e$ molecules simplifies the analysis. Such a system will reach equilibrium when the number of molecules excited by a single pulse is equal to the number of molecules that return to the ground state over the time interval equal the 1/RR. So for a given RR, the number of excited molecules returning to the ground state between pulses is simply the difference between the total number of molecules in the excited state immediately after the pulse arrival, $N_{eT}$, and the total number of molecules in the excited state after time 1/RR (the time when next pulse arrive):

$$N_e = N_{eT} - N_{eT} e^{-1/\tau \cdot RR} = N_{eT}(1 - e^{-1/\tau \cdot RR}) \qquad (1)$$

where $\tau$ is the fluorescence lifetime of the fluorophore. For simplicity of the model it's possible to assume that the fluorophore has a single exponential decay. One can also calculate the number of molecules in the excited state by analyzing subsequent pulses. The first pulse excites $N_e$ molecules. When the second pulse arrives, the number of molecules remaining in the excited state is $N_1 = N_e e^{-/\tau \cdot RR}$ and total number of excited molecules immediately after second pulse is: $N_e^1 = N_1 + N_e$. Extending this for n pulses, there is a geometrical series, and the number of molecules in the exited state after n pulses will be:

$$N_{eT}^n = N_e \frac{1 - e^{-n/\tau \cdot RR}}{1 - e^{-1/\tau \cdot RR}} \qquad (2)$$

And consequently for an infinite number of pulses:

$$N_{eT} = \frac{N_e}{1 - e^{-1/\tau \cdot RR}} \qquad (3)$$

That is identical to the equilibrium solution given by Equation (1). In FIG. 1a the number of excited molecules after 5 pulses for three model fluorophores with fluorescence lifetimes of 4 ns, 10 ns, and 100 ns as a function of increasing RR from 1 MHz to 100 MHz. For comparison, in FIG. 1b the relative number of molecules in the excited state for equilibrium conditions (after an infinite number of pulses). Thus, the number of molecules in the excited state after each pulse for a short-lived fluorophore is constant and for a long-lived fluorophore increases quickly with the RR. It is important to realize that for a continuous train of pulses, the out coming intensity of fluorescence (number of emitted photons) depends on the decay factor $e^{-1/\tau RR}$ and the relative average intensities for short-lived and long-lived fluorophores are increasing proportionally with increasing RR. The intensity is not only proportional to the number of molecules in the excited state at the instant of each excitation pulse but also to the interval between pulses. In steady-state conditions, the relative intensities must be the same—increasing the RR cannot change the relative signals of two fluorophores. However, the situation changes dramatically when using a different approach. The present invention uses variable pulse trains that allow time for the excited states to depopulate completely after a series of pulses (burst of pulses). By detecting only the fluorescence intensity decay after the last pulse in the burst, it is possible to dramatically change the relative intensities of long-lived probe to a short-lived background. Depending on the ratio between T and 1/RR, the initial population of the excited state will be different, resulting in a different number of photons collected after the last pulse in the burst. This is illustrated in the example shown in FIG. 2 with a 10-pulse burst and $\tau^*RR=0.32$, 0.80, and 8.00. Assuming that RR=80 MHz, which is commonly available in pulsed diode lasers, these ratios would correspond to $\tau=4$ ns, 10 ns, and 100 ns, respectively. The total fluorescence from each model dye measured over the entire time interval shown will be the result of exactly 10 excitation-decay cycles regardless of the $\tau^*RR$ factor. However, the 4 ns dye decays almost completely between excitation pulse, and each cycles is practically completed before the arrival of the next pulse. For 10 ns and 100 ns dyes, there is significant overlap with each excitation cycle. If only fluorescence decay is measure after the last excitation pulse, this measurement for the 10 ns and 100 ns dyes will include the fluorescence from the overlapping excited state population from previous excitation pulses in the burst. Thus, it is this break between bursts of excitation pulses that we may exploit in order to increase the contrast between fluorophores of differing decay times. Thus, for a fixed RR (fixed pulse separation in the burst), an increased lifetime results in a greater relative signal for the long-lived dye. If the fluorescence lifetime is much longer than the separation of pulses in the burst (1/RR), the number of long-lived fluorophores in the excited states after a small number of pulses is proportional to that number of pulses. As such, for a pulse repetition of 80 MHz within the burst and a dye with a fluorescence lifetime of 200 ns or more (like some metal-ligand complexes), the number of dyes in the excited state after 10 pulses is ~10 times greater than that for a single pulse. In the same time, the number of background fluorophores in the exited state that have a fluorescence lifetime of 2 ns will be almost constant from pulse-to-pulse (the fluorophores will decay completely within 12.5 ns interval time). In effect, synchronizing the time correlated detection with the last pulse in the burst will give ~10 times greater signal than that from each individual pulse. The present method is both conceptually and physically very different from simply increasing the power delivered by single pulses 10-fold, in which case both populations (short-lived background and long-lived dye) increase proportionally (5 times in this case).

In one example, laser excitation was provided by a pulsed laser diode (PDL-470) emitting 470 nm light and driven by a PDL 828 "Sepia II" driver. This driver was operated at 80 MHz and configured so that the pulse train consisted of bursts of laser pulses with 80 MHz RR and followed by a series of blank "pulses." In the case of conventional, single pulse excitation, one pulse from the 470 nm diode laser was followed by 249 blank pulses, exciting the sample with an effective repetition rate of 320 kHz. For the case of excitation by a burst of m pulses, the burst would be followed by 250-m blank pulses, so that the total pulse train remained 250 pulses long, or 3.125 μs in length. Because the base oscillator operated at 80 MHz, there were 12.5 ns between each excitation pulse. In order to differentiate the advantageous pumping of long-lived dyes from the increased intensity that simply results from increased repetition rate of the excitation source, only the fluorescence following the final excitation pulse was analyzed. For example, when 10 pulses were used, the final pulse arrived 129 ns after the synchronization pulse from the laser driver. So only photons arriving between 129 ns and the end of the synchronization period at 2100 ns were analyzed. The effective synchronization period was therefore 1971 ns, and this was kept constant for all excitation schemes. However, the effective synchronization period was shifted to start at the peak of the last pulse in the excitation burst. FIG. 3 shows a schematic of the excitation schemes for 3 burst lengths (1 pulse, 5 pulses, and 10 pulses).

Measurements were performed on a MicroTime 200 time-resolved, confocal microscope. The excitation and emission light was focused by a 60× 1.2 NA Olympus objective in an Olympus IX71 microscope, and the emission light was filtered by a 488 long wave pass filter before passing through a 50 µm pinhole. Detection was made by a hybrid photomultiplier assembly. The resolution of the time correlated single photon counting (TCSPC) module was set to 512 ps/bin in order to facilitate the detection of the long-lived Ruthenium dye, producing a measurement window around 1.2 µs in length. However, the resolution was increased to 16 ps/bin when the lifetimes of Sulforhodamine B were measured (FIG. 4), as the short lifetime of this dye cannot be accurately measured otherwise. All data analysis was performed on the SymPhoTime software, version 5.3.2. All equipment and the SymPhoTime software were provided by PicoQuant, GmbH as part of the MicroTime 200 system. The surface plots in FIGS. 7a-j were created using ImageJ software.

Samples were prepared using aqueous solutions of the Ruthenium based dye Tris(2,2'-bipyridyl)dichlororuthenium (II) hexahydrate (Ru) (Sigma-Aldrich) and Sulforhodamine B (SRB) dropped onto a No. 1 coverslip from Thermo Electron. The confocal volume was positioned so that it was 20 µm above the top surface of the coverslip. When imaging was involved, beads labeled with absorbed Ru dye were mixed into an aqueous solution of polyvinyl alcohol (Sigma-Aldrich), and dropped onto a heated coverslip to dry quickly. Then the solution of SRB was dropped near the dried droplet of Ru. The images were taken at the interface of these two droplets, where the two substances had mixed.

Figure 4:
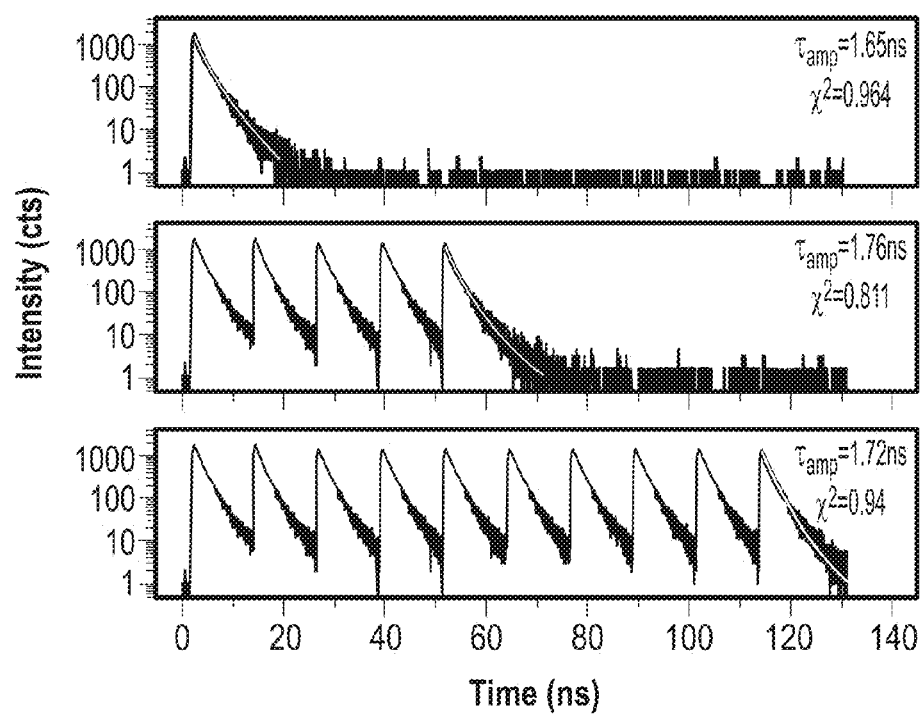
FIG. 4 shows three intensity decays of a SRB solution with 1-pulse, 5-pulse, and 10-pulse excitation schemes. No appreciable change is seen in the lifetime fittings.

The dyes were chosen to show a simple example of the contrast improvements that can be achieved with multi-pulse excitation. As shown in FIG. 4, the lifetime of SRB was ~1.7 ns, and did not change appreciably between 1-pulse, 2-pulse, and 5-pulse excitation schemes. It was also found that the intensity of the fluorescence signal did not increase with each pulse, as the short-lived dye decays nearly completely in the 12.5 ns between subsequent pulses.

Figure 5:
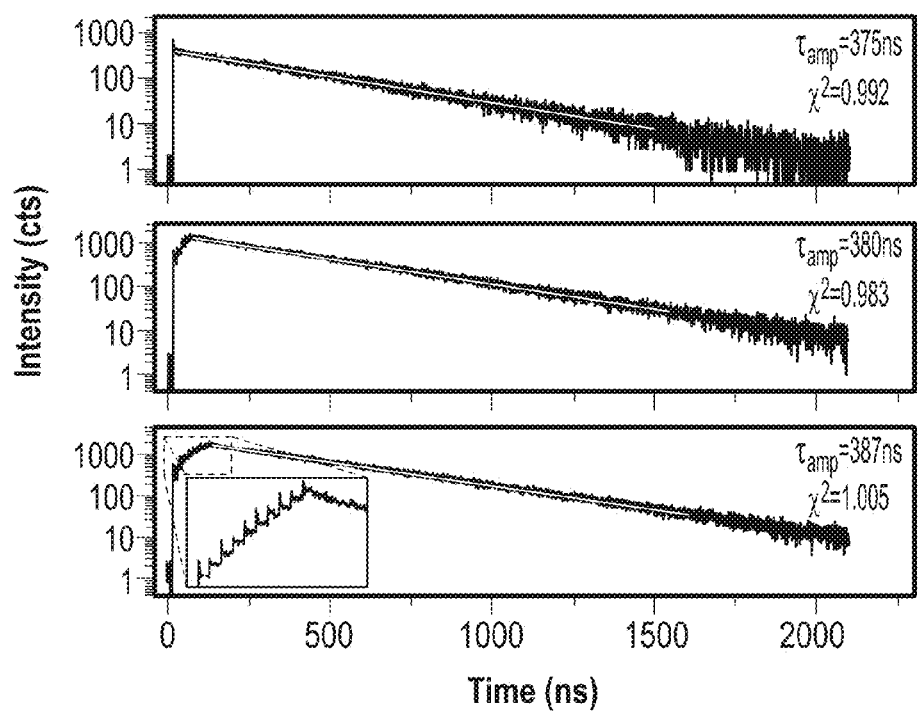
FIG. 5 shows three intensity decays of a Ru dye solution with 1-pulse, 5-pulse, and 10-pulse excitation schemes. No appreciable change is seen in the lifetime fittings. The time scale of this figure is set very large in order to accommodate the ~380 ns liftime of Ru, however, the inset in the bottom graph shows a magnified view of the excited state pumping that occurs with the 10-pulse excitation. Both the time scales and intensity scales of the inset are linear.
Figure 6:
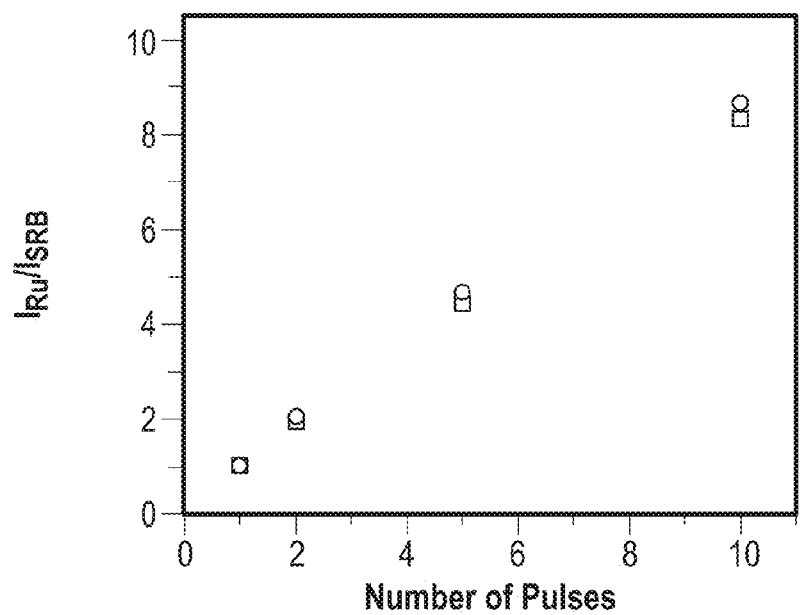
FIG. 6 is graph that shows an increasing signal to background intensity with multi-pulse excitation. The squares represent the intensities collected from the short-lived SRB, and the circles represent the intensities collected from the long-lived Ru. Both were measured from pure, aqueous solutions of the individual dyes. Error bars are shown on the experimental data to portray the standard deviation between 3 collections, which was always less than 2%.

FIG. 5 shows the results of the same experiment conducted on Ru dye. Just as with SRB, the lifetime of this dye was also independent of the number of excitation pulses applied. Please note that the time scale has been expanded to accommodate the long-lived dye. However, this long-lived dye experienced a dramatic pumping effect with the addition of multiple excitation pulses. The inset of the 5-pulse decay curve shows the pumping on a linear scale. In the manner described in the previous section, the total fluorescence intensity was measured from 1-pulse, 2-pulse, 5-pulse, and 10-pulse excitation schemes, and the results are shown in FIG. 6. The data are normalized to the single pulse intensity of each respective dye. FIG. 6 shows the dramatic increase in relative intensity of Ru dye with increasing number of pulses in the burst which begins to level off between burst lengths of 5 and 10 pulses.

Figures 7A, 7B, 7C, 7D, 7E:
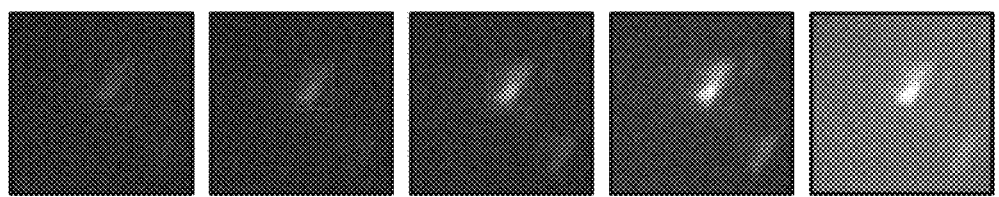
FIGS. 7a to 7j show fluorescence imaging with multiple pulse excitation.
Figures 7F, 7G, 7H, 7I, 7J:
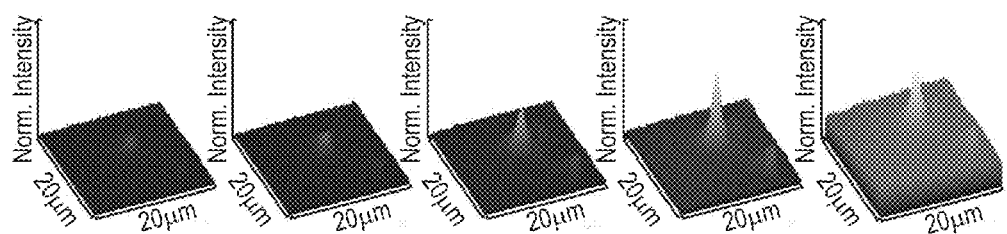
Figure 8A:
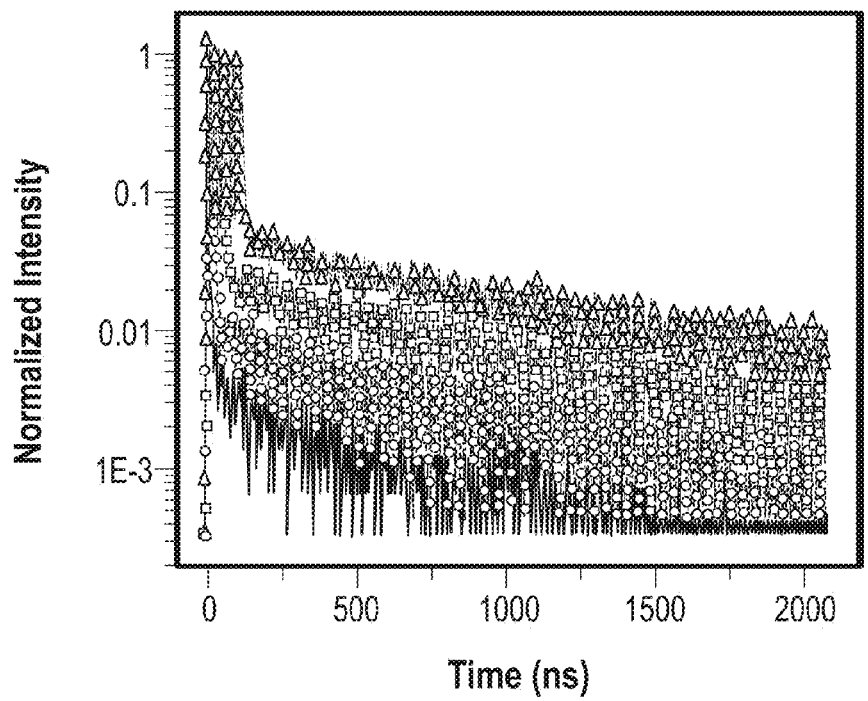
FIGS. 8a and 8b shows fluorescence intensity decays collected from the area indicated in the white boxes in FIGS. 7a through 7d. The solid line shows 1 pulse excitation, circles show 2-pulse excitation, squares show 5-pulse excitation, and triangles show 10-pulse excitation. All data are normalized to the last pulse in the burst.
Figure 8B:
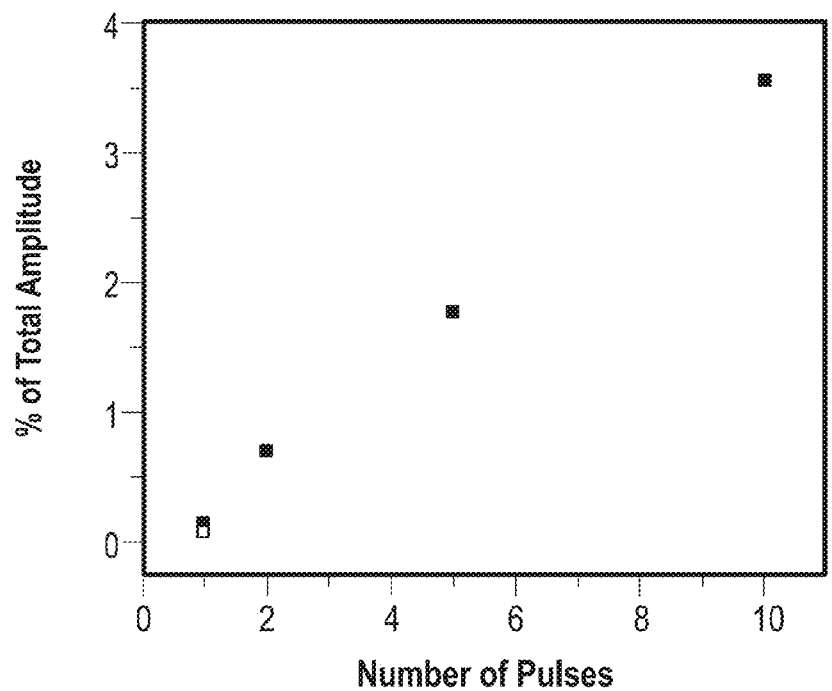

As an example of multi-pulse excitation for imaging, a Ru-loaded bead positioned on a background of SRB was prepared. The image shows improved contrast of the Ru bead as excitation is increased from 1 pulse to 2, 5, and 10 pulses. The corresponding surface plots below further highlight the increased contrast. Note that the surface plots are normalized to the peak intensity of the 10-pulse excitation image in FIG. 7d. It was found that the increase in intensity from the Ru loaded bead was proportional to the number of pulses in the burst. The laser driver was reconfigured for 1-pulse excitation and increased the output power (average energy delivered per second) to equal the power employed in the 10-pulse excitation scheme, so that one strong laser pulse would deliver the same energy as 10 weaker pulses. Then an image was collected from the same region, which is shown in FIG. 7e. It is important to note how the more powerful, single pulse, was capable of producing the same signal from the Ru bead. However, the SRB background was dramatically increased in FIG. 7e compared to FIG. 7d. Thus the multi-pulse excitation scheme of the present invention significantly improved the signal to background ratio. A region of interest (ROI) was selected on the bead and analyzed intensity decays from 1-pulse, 2-pulse, 5-pulse, and -10 pulse excitation. The intensity decays are presented in FIGS. 8a and 8b. For all excitation schemes, a significant short-lived decay component from the background is detected. This is expected since the bead is emerged in the short-lived SRB background. As the number of pulses increased, FIG. 8a shows that the long-lived decay component rose and the relative contribution of the short-lived component decreased.

The present inventors show that a simple burst of pulses can be used to change the relative intensities of components with different lifetimes. When the probe has a significantly longer lifetime than the background, the relative intensity of the probe can be dramatically increased by increasing the number of pulses and decreasing the pulse separation in each burst. In practice with a fundamental repetition rate of 80 MHz, it is now possible to increase the relative intensity of a probe that has fluorescence lifetime of 20 ns over 100% by just using 5 pulses burst and still keep a 1-5 MHz effective repetition rate for the bursts that is convenient for fast imaging. Using a laser system with a fundamental repetition rate of 200 MHz, the same 20 ns probe would be enhanced over 300% as compared to the background.

This measurement scheme is very advantageous for, e.g., extremely long-lived fluorophores like lanthanide probes, where the lifetimes are in the microsecond to millisecond range, which may also be used with the present invention. Such systems are typically used with time-gated detection to eliminate the background. In this case, using a high repetition rate system and a burst excitation scheme allows increasing of the initial intensity of the probe without increasing the background intensity, all while still allowing time-gated detection.

Finally how pulse bursts may affect photostability was measured. Using 5 pulses in place of one 5 times stronger does not change relative photostability of the probe as compared to the background photostability. Thus, using weaker multiple pulses produces less local heating and promote better photostability.

Figure 9:
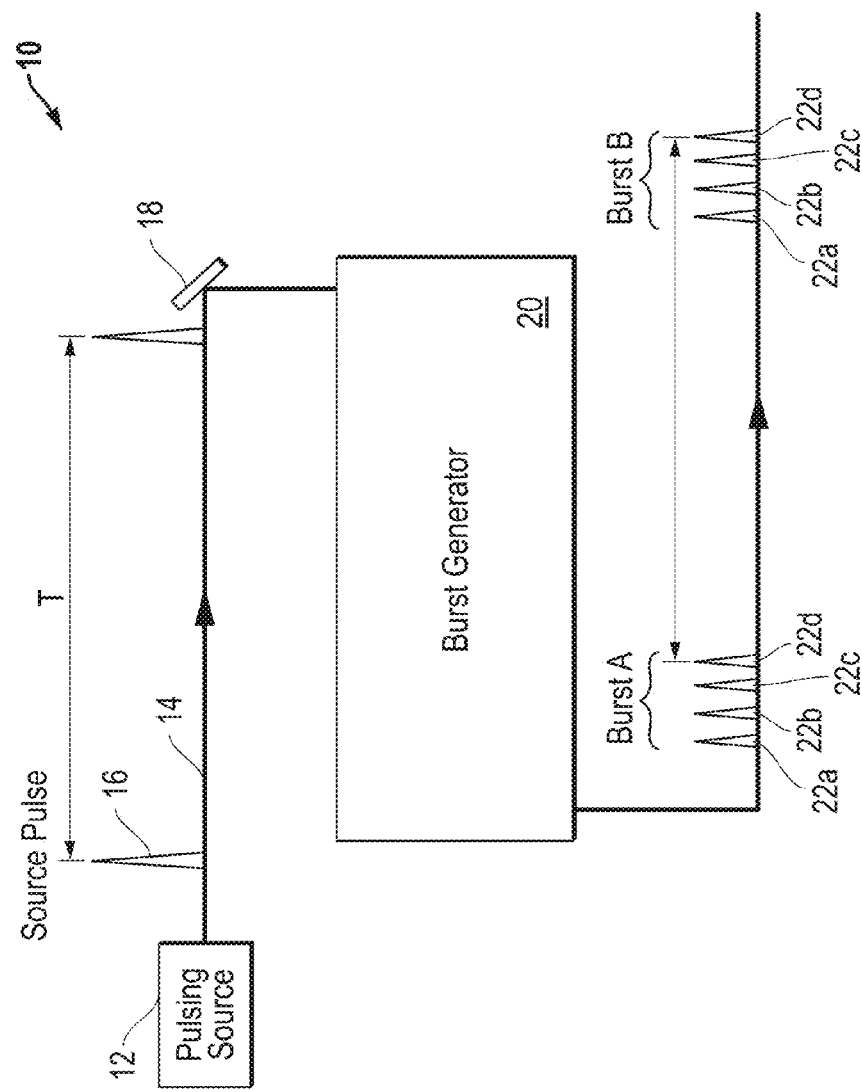
FIG. 9 shows an example of a basic schematic for a burst generator.

FIG. 9 shows one example of a schematic of a burst pulse generator 10 for use with the present invention. A pulsing source 12 generates light 14 in the form of a source pulse 16 separated by time T. The light 14 strikes a mirror 18 and enters a burst generator 20 that generates burst packets A, B shown as pulses 22a, 22b, 22c and 22d.

Figure 10:
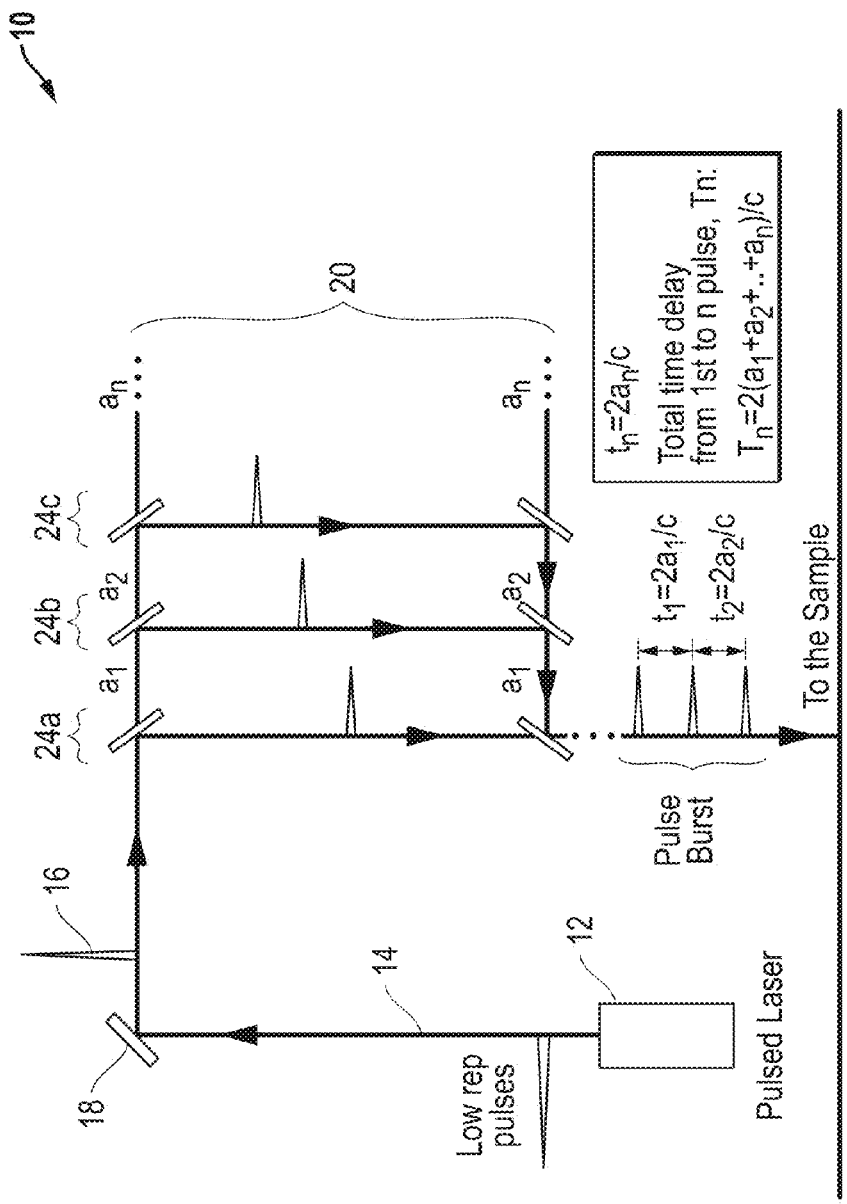
FIG. 10 shows the example of an optical system based on optical delays for burst generator. Each semitransparent mirror separates part of the pulse and send it through the different optical path. Differently delayed pulses are combined before entering or entering the sample.

FIG. 10 shows the example of an optical system based on optical delays for burst pulse generator 10. Each semitransparent mirror separates part of the pulse and send it through the different optical path. Differently delayed pulses are combined before entering or entering the sample. A pulsing source 12 generates light 14 in the form of a source pulse 16 separated by time T. The light 14 strikes a mirror 18 and enters a burst generator 20 that includes multiple mirror pairs 24a, 24b, 24c that are separated by a distance $a_1$, $a_2$, etc., that form the pulses.

Figure 11:
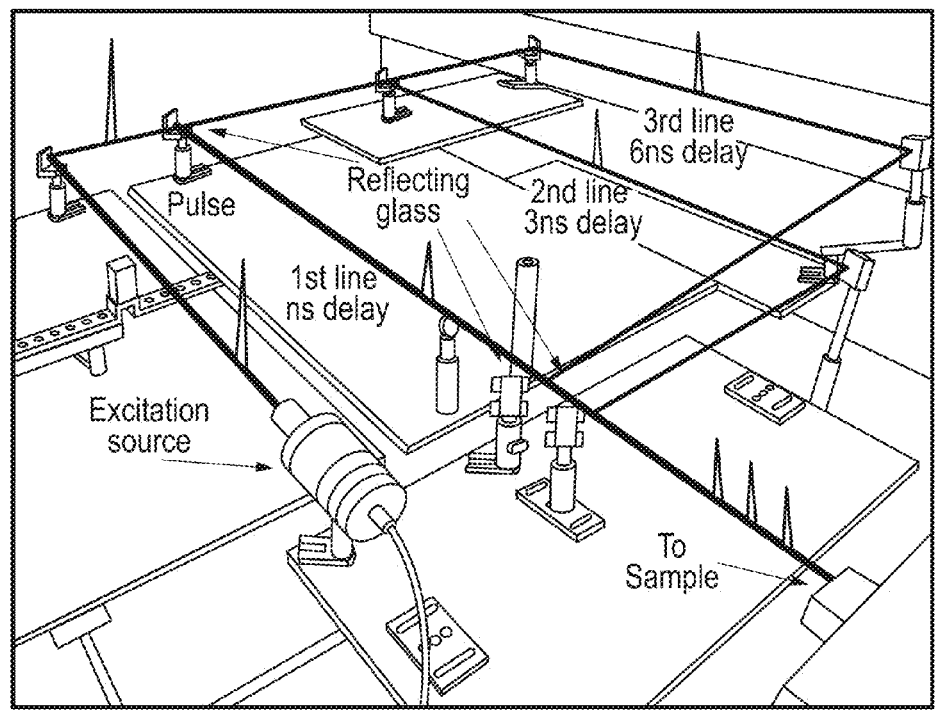
FIG. 11 shows a photograph of optical pulse generator build for 3 pulses burst.

FIG. 11 shows a photograph of optical pulse generator build for 3 pulses burst.

Figure 12:
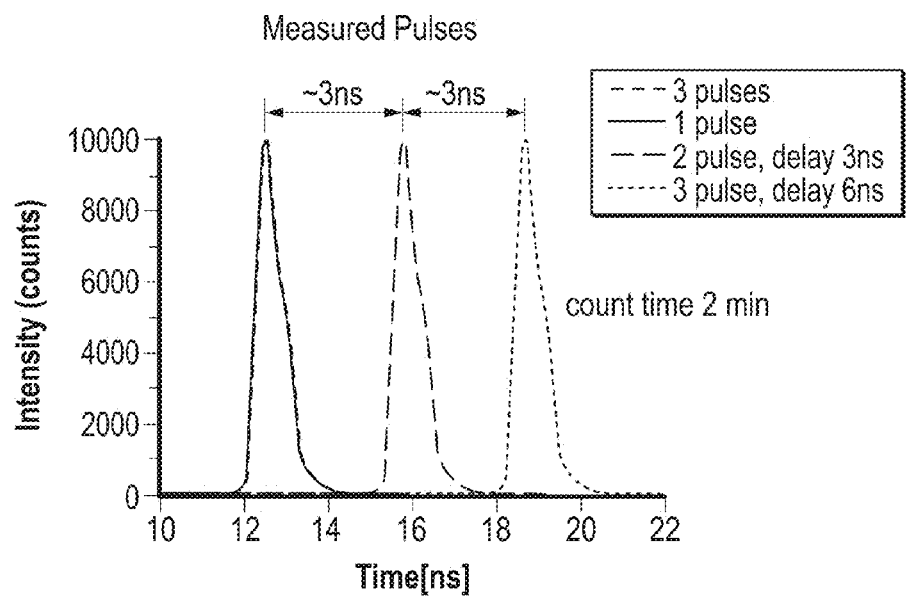
FIG. 12 shows the example of 3 pulses detected. The Figure contains each pulse detected individually and all 3 simultaneously overlaid with the solid or dashed lines as shown.

FIG. 12 shows the example of 3 pulses detected. The Figure contains each pulse detected individually and all 3 simultaneously overlaid with solid or dashed lines as shown.

Figures 13A, 13B:
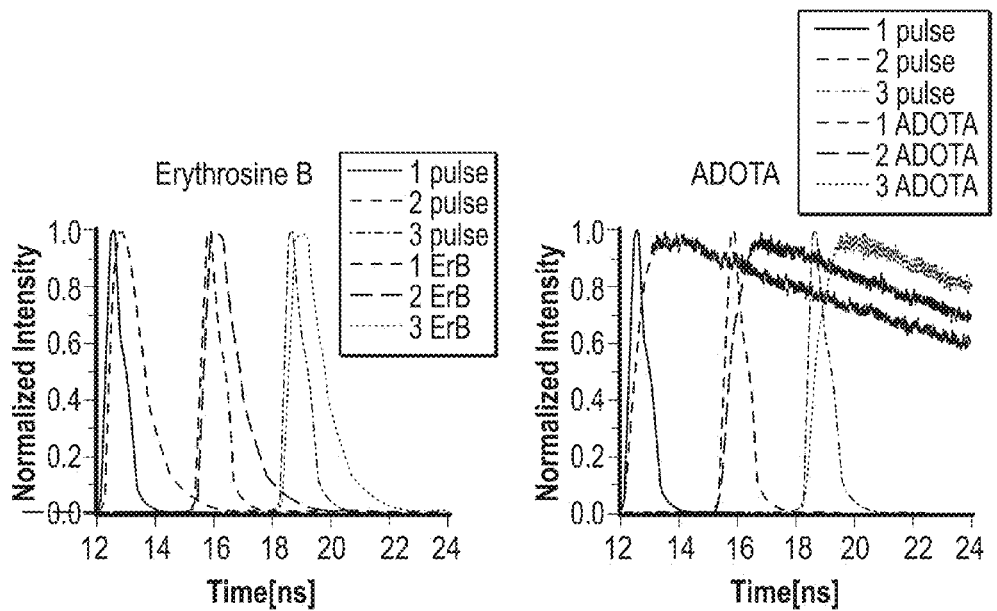
FIGS. 13a and 13b show the example of detected signals—intensity decays for short-lived Erythrosine B (ErB) with ~0.4 ns fluorescence lifetime and longer-lived ADOTA probe with ~20 ns fluorescence lifetime excited with each individual pulse.

FIGS. 13a and 13b show the example of detected signals—intensity decays for short-lived Erythrosine B (ErB) with ~0.4 ns fluorescence lifetime and longer-lived ADOTA probe with ~20 ns fluorescence lifetime excited with each individual pulse.

Figure 14:
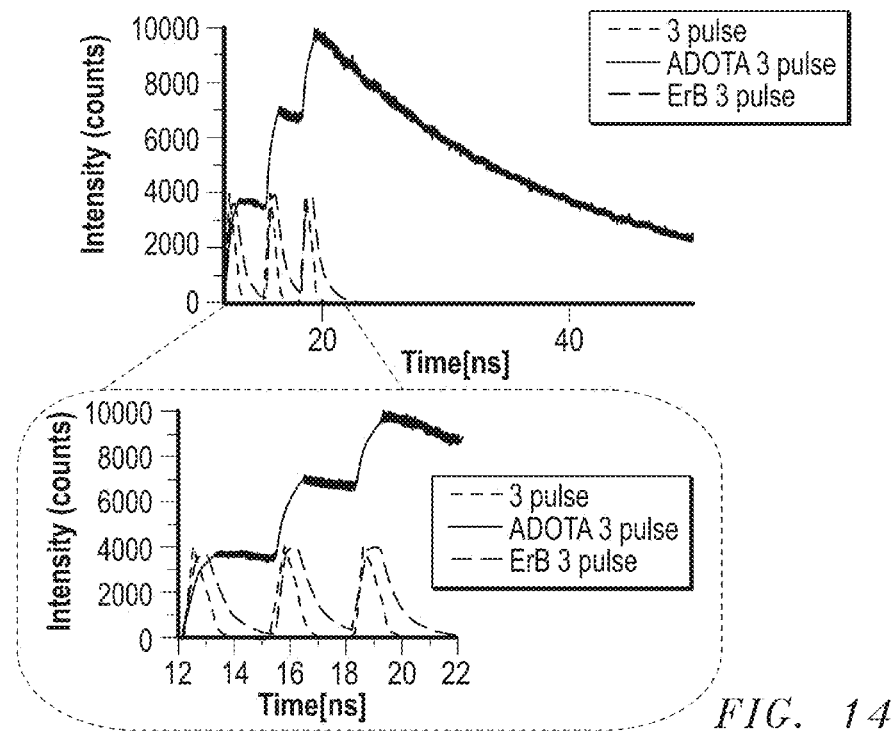
FIG. 14 shows the signal detected for both dyes—ErB and ADOTA with 3 consecutive pulses in the burst.

FIG. 14 shows the signal detected for both dyes—ErB and ADOTA with 3 consecutive pulses in the burst.

Figure 15:
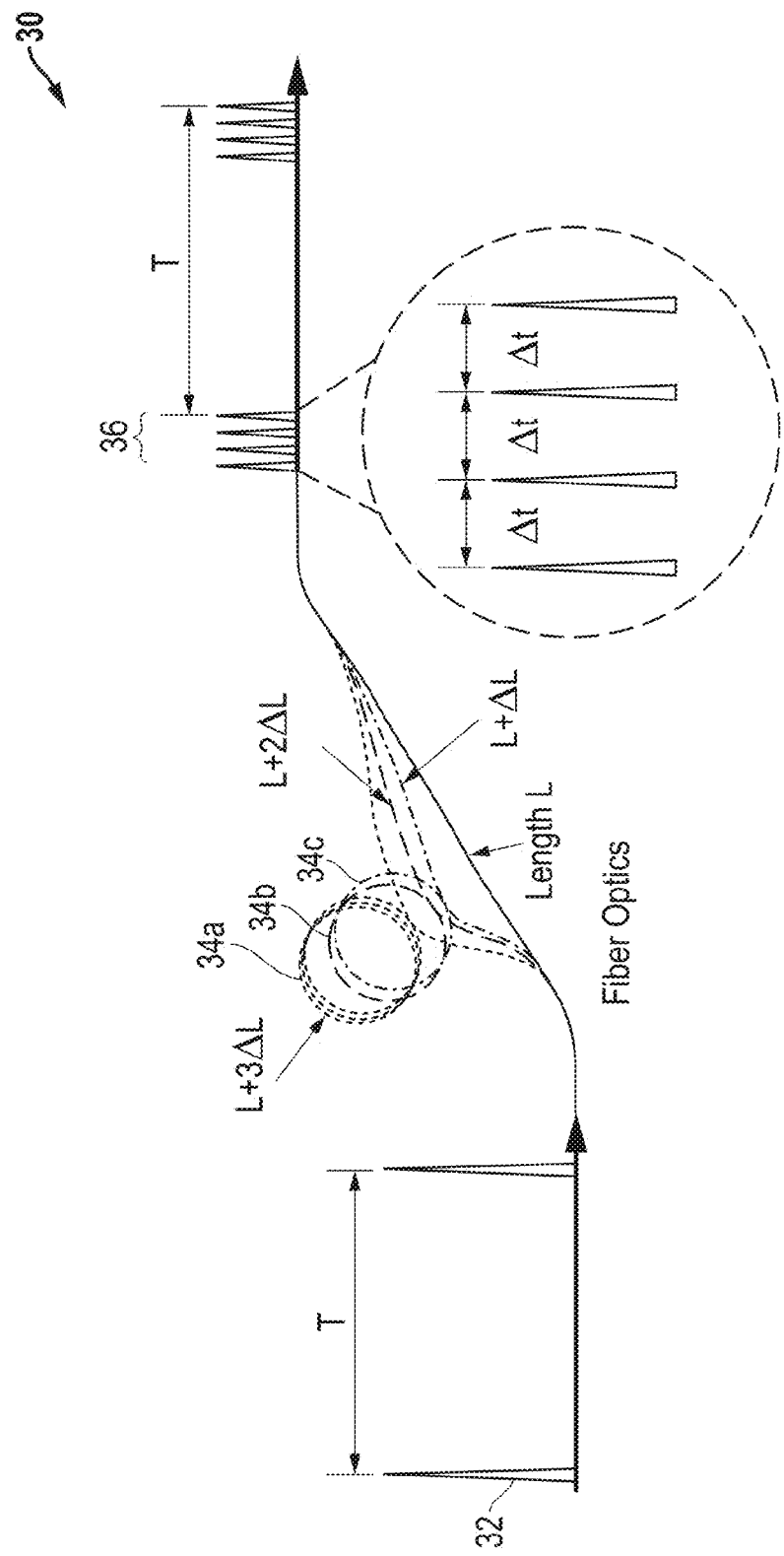
FIG. 15 shows the graphical concept for fiber optics based burst generator. A single pulse is divided to n fiber optics of different length each and recombined before or entering the sample.

FIG. 15 shows the graphical concept for fiber optics based burst generator 30. A single pulse 32 is divided to n fiber optics 34a, 34b, 34c, of different length each, and recombined before or entering the sample to form the burst of pulses 36 separated by time T.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

[1] M. Funovics, R. Weissleder, C.-H. Tung, Protease sensors for bioimaging, Anal. Bioanal. Chem. 377 (2003) 956-963.

[2] R. Y. Tsien, Building and breeding molecules to spy on cells and tumors, Febs Lett. 579 (2005) 927-932.

[3] M. Yang, E. Baranov, P. Jiang, F.-X. Sun, X.-M. Li, L. Li, et al., Whole-body optical imaging of green fluorescent protein-expressing tumors and metastases, Proc. Natl. Acad. Sci. 97 (2000) 1206-1211.

[4] M. Yang, E. Baranov, A. R. Moossa, S. Penman, R. M. Hoffman, Visualizing gene expression by whole-body fluorescence imaging, Proc. Natl. Acad. Sci. 97 (2000) 12278-12282.

[5] F. Leblond, S. C. Davis, P. A. Valdés, B. W. Pogue, Pre-clinical whole-body fluorescence imaging: Review of instruments, methods and applications, J. Photochem. Photobiol. B. 98 (2010) 77-94.

[6] R. M. Rich, M. Mummert, Z. Gryczynski, J. Borejdo, T. J. Sørensen, B. W. Laursen, et al., Elimination of autofluorescence in fluorescence correlation spectroscopy using the AzaDiOxaTriAngulenium (ADOTA) fluorophore in combination with time-correlated single-photon counting (TCSPC), Anal. Bioanal. Chem. 405 (2013) 4887-4894.

[7] S. Ghisla, V. Massey, J.-M. Lhoste, S. G. Mayhew, Fluorescence and optical characteristics of reduced flavines and flavoproteins, Biochemistry (Mosc.). 13 (1974) 589-597.

[8] A. C. Croce, A. Spano, D. Locatelli, S. Barni, L. Sciola, G. Bottiroli, Dependence of Fibroblast Autofluorescence Properties on Normal and Transformed Conditions. Role of the Metabolic Activity, Photochem. Photobiol. 69 (1999) 364-374.

[9] N. M. Haralampus-Grynaviski, L. E. Lamb, C. M. R. Clancy, C. Skumatz, J. M. Burke, T. Sarna, et al., Spectroscopic and morphological studies of human retinal lipofuscin granules, Proc. Natl. Acad. Sci. 100 (2003) 3179-3184.

[10] S. A. Schnell, W. A. Staines, M. W. Wessendorf, Reduction of Lipofuscin-like Autofluorescence in Fluorescently Labeled Tissue, J. Histochem. Cytochem. 47 (1999) 719-730.

[11] B. Clancy, L. Cauller, Reduction of background autofluorescence in brain sections following immersion in sodium borohydride, J. Neurosci. Methods. 83 (1998) 97-102.

[12] T. Cowen, A. J. Haven, G. Burnstock, Pontamine sky blue: A counterstain for background autofluorescence in fluorescence and immunofluorescence histochemistry, Histochemistry. 82 (1985) 205-208.

[13] D. Schweitzer, E. R. Gaillard, J. Dillon, R. F. Mullins, S. Russell, B. Hoffmann, et al., Time-Resolved Autofluorescence Imaging of Human Donor Retina Tissue from Donors with Significant Extramacular Drusen, Invest. Ophthalmol. Vis. Sci. 53 (2012) 3376-3386.

[14] W. Becker, Fluorescence lifetime imaging—techniques and applications, J. Microsc. 247 (2012) 119-136.

[15] H. Schneckenburger, M. Wagner, P. Weber, W. S. L. Strauss, R. Sailer, Autofluorescence Lifetime Imaging of Cultivated Cells Using a UV Picosecond Laser Diode, J. Fluoresc. 14 (2004) 649-654.

[16] R. M. Rich, D. L. Stankowska, B. P. Maliwal, T. J. Sørensen, B. W. Laursen, R. R. Krishnamoorthy, et al., Elimination of autofluorescence background from fluorescence tissue images by use of time-gated detection and the AzaDiOxaTriAngulenium (ADOTA) fluorophore, Anal. Bioanal. Chem. 405 (2013) 2065-2075.

[17] S. V. Eliseeva, J.-C. G. Bünzli, Lanthanide luminescence for functional materials and bio-sciences, Chem. Soc. Rev. 39 (2009) 189-227.

[18] D. Jin, J. A. Piper, Time-Gated Luminescence Microscopy Allowing Direct Visual Inspection of Lanthanide-Stained Microorganisms in Background-Free Condition, Anal. Chem. 83 (2011) 2294-2300.

[19] R. Rich, J. Li, R. Fudala, Z. Gryczynski, I. Gryczynski, W. Mandecki, Properties of coatings on RFID p-Chips that support plasmonic fluorescence enhancement in bioassays, Anal. Bioanal. Chem. 404 (2012) 2223-2231.

[20] J. R. Lakowicz, H. Szmacinski, K. Nowaczyk, K. W. Berndt, M. Johnson, Fluorescence lifetime imaging, Anal. Biochem. 202 (1992) 316-330.

[21] R. Pepperkok, A. Squire, S. Geley, P. I. H. Bastiaens, Simultaneous detection of multiple green fluorescent proteins in live cells by fluorescence lifetime imaging microscopy, Curr. Biol. 9 (1999) 269-274.

[22] D. S. Bilan, L. Pase, L. Joosen, A. Y. Gorokhovatsky, Y. G. Ermakova, T. W. J. Gadella, et al., HyPer-3: A Genetically Encoded H2O2 Probe with Improved Performance for Ratiometric and Fluorescence Lifetime Imaging, Acs Chem. Biol. 8 (2013) 535-542.

[23] R. Beams, D. Smith, T. Johnson, S.-H. Oh, L. Novotny, N. Vamivakas, Using a Single Diamond NV Center for Nanoscale Fluorescence Lifetime Imaging, in: Rochester Conf. Coherence Quantum Opt. Quantum Inf. Meas. Meet., Optical Society of America, 2013: p. M6.55.

[24] B. K. Muller, E. Zaychikov, C. Brauchle, D. C. Lamb, Pulsed Interleaved Excitation, Biophys. J. 89 (2005) 3508-3522.

[25] S. Fore, Y. Yuen, L. Hesselink, T. Huser, Pulsed-Interleaved Excitation FRET Measurements on Single Duplex DNA Molecules Inside C-Shaped Nanoapertures, Nano Lett. 7 (2007) 1749-1756.

[26] S. Rüttinger, R. Macdonald, B. Krämer, F. Koberling, M. Roos, E. Hildt, Accurate single-pair Förster resonant energy transfer through combination of pulsed interleaved excitation, time correlated single-photon counting, and fluorescence correlation spectroscopy, J. Biomed. Opt. 11 (2006) 024012-024012.

[27] G. Sánchez-Mosteiro, E. M. H. P. van Dijk, J. Hernando, M. Heilemann, P. Tinnefeld, M. Sauer, et al., DNA-Based Molecular Wires: Multiple Emission Pathways of Individual Constructs, J. Phys. Chem. B. 110 (2006) 26349-26353.

What is claimed is:

1. A method for enhancing the signal-to-noise ratio from an emission comprising:
   selecting a probe capable of at least one of fluorescence, phosphorescence, or delayed fluorescence in or about a sample that comprises interfering background signal; and
   exposing the probe to one or more controllable bursts, each burst comprising two or more high repetition energy pulses, wherein the pulses are timed to allow time for excited states of molecules in the probe to depopulate complete after a series of pulses,
   wherein the one or more controllable bursts of high repetition energy pulses enhance the signal from the probe above that of the background signal.

2. The method of claim 1, wherein the probe is selected from the group of long-lived emitters like ADOTA group of dyes, pyrene and dansyl type emitters, porphyrins based dyes, lanthanides probes, metal-ligand complex probes like ruthenium probes, quantum dots, or quantum nanomaterials, nanodiamonds; also probes 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CF SE; Calcein; Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone; and Yellow fluorescent protein.

3. The method of claim 1, wherein the probe is exposed to 2, 3, 4, 5, 6, 7, 8, 9, 10, 11, 12, 13, 14, 15, 20, 25, 30, 35, 40, 45, 50, 100, 200, 300, 400, 500, 750, 1,000, $10^5$, $10^6$, $10^7$ or more burst trains before, during or prior to detection.

4. The method of claim 1, wherein each of the one or more bursts comprises 2, 3, 4, 5, 6, 7, 8, 9, 10, 11, 12, 13, 14, 15, 20, 25, 30, 35, 40, 45, 50, 100, 200, 300, 400, 500, 750, 1,000 pulses before, during or prior to detection.

5. The method of claim 1, wherein the frequency in bursts is higher than the repetition of the burst.

6. The method of claim 1, wherein each of the bursts, the pulses, or both are of a different wavelength.

7. The method of claim 1, wherein the number of pulses in a burst is variable.

8. The method of claim 1, wherein the pulses are spaced as one or more low repetition packets.

9. The method of claim 1, wherein the time between bursts is timed to optimize the detection of the probe.

10. The method of claim 1, wherein the time between bursts is larger than the time between pulses in each burst.

11. The method of claim 1, further comprising the step of detecting the signal from the probe.

12. The method of claim 1, further comprising the step of detecting the signal from the probe and wherein detection of the signal from the probe is as least one of a time-gated or time-delayed detection.

13. The method of claim 1, wherein the pulses have a controllable bursts comprise a range from 1 kHz up to the repetition rate of the pulses in a burst.

14. The method of claim 1, wherein the pulse duration can be from femtoseconds (Ti: Sapphire type lasers), picosecond (laser diodes, dye lasers, and Sapphire lasers), nanoseconds (Nitrogen or Argon lasers), pulsed laser diodes and light emitting diodes (with pulse duration from picosecond to milliseconds).

15. The method of claim 1, wherein the background signal is from at least one of a cell, a tissue, a cellular sample or tissue sample on a slide, an organ or whole animal, a human organ, tissue, or whole body imaging.

16. The method of claim 1, wherein the background signal is from at least one of a diagnostic test, a solvent, a DNA array, a RNA array, a gel, paper, a cellulose, or a supporting matrix.

17. The method of claim 1, wherein the background signal has a shorter lifetime that the probe.

18. The method of claim 1, further comprising the step of imaging the fluorescence, phosphorescence, or delayed fluorescence from the sample.

19. The method of claim 1, further comprising the step of imaging the fluorescence, phosphorescence, or delayed fluorescence from a virus, bacterial, fungi, plant, animal, or human.

20. An apparatus for enhancing the signal-to-noise ratio from an emission comprising:
a source of electromagnetic radiation capable of exciting a probe selected from at least one of fluorescence, phosphorescence, or delayed fluorescence, in or about a sample having an interfering background signal, wherein the source is capable of delivering one or more controllable bursts, each of the bursts comprising two or more pulses, wherein the pulses are timed to allow time for excited states of molecules in the probe to depopulate completely after a series of pulses,
wherein the one or more controllable bursts of pulses contact and excite the probe in or about the sample to enhance the signal from the probe above that of the background signal.

21. The apparatus of claim 20, wherein the probe is selected from the group of long-lived emitters like ADOTA group of dyes, pyrene and dansyl type emitters, porphyrins based dyes, lanthanides probes, metal-ligand complex probes like ruthenium probes, quantum dots, or quantum nanomaterials, nanodiamonds; also probes 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CF SE; Calcein; Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone; and Yellow fluorescent protein.

22. The apparatus of claim 20, wherein the probe is exposed to 2, 3, 4, 5, 6, 7, 8, 9, 10, 11, 12, 13, 14, 15, 20, 25, 30, 35, 40, 45, 50, 100, 200, 300, 400, 500, 750, 1,000, $10^5$, $10^6$, $10^7$ or more burst trains before, during or prior to detection.

23. The apparatus of claim 20, wherein each of the one or more bursts comprises 2, 3, 4, 5, 6, 7, 8, 9, 10, 11, 12, 13, 14, 15, 20, 25, 30, 35, 40, 45, 50, 100, 200, 300, 400, 500, 750, 1,000 pulses before, during or prior to detection.

24. The apparatus of claim 20, wherein the frequency in bursts is higher than the repetition of the burst.

25. The apparatus of claim 20, wherein each of the bursts, the pulses, or both are of a different wavelength.

26. The apparatus of claim 20, wherein the number of pulses in a burst is variable.

27. The apparatus of claim 20, wherein the pulses are spaced as one or more low repetition packets.

28. The apparatus of claim 20, wherein the time between bursts is timed to optimize the detection of the probe.

29. The apparatus of claim 20, wherein the time between bursts is larger than the time between pulses in each burst.

30. The apparatus of claim 20, further comprising the step of detecting the signal from the probe.

31. The apparatus of claim 20, further comprising the step of detecting the signal from the probe and wherein detection of the signal from the probe is as least one of a time-gated or time-delayed detection.

32. The apparatus of claim 20, wherein the pulses have a controllable bursts comprise a range from 1 kHz up to the repetition rate of the pulses in a burst.

33. The apparatus of claim 20, wherein the pulse duration can be from femtoseconds (Ti:Sapphire type lasers), picosecond (laser diodes, dye lasers, and Sapphire lasers), nanoseconds (Nitrogen or Argon lasers), pulsed laser diodes and light emitting diodes (with pulse duration from picosecond to milliseconds).

34. The apparatus of claim 20, wherein the background signal is from at least one of a cell, a tissue, a cellular sample or tissue sample on a slide, an organ or whole animal, a human organ, tissue, or whole body imaging.

35. The apparatus of claim 20, wherein the background signal is from at least one of a diagnostic test, a solvent, a DNA array, a RNA array, a gel, paper, a cellulose, or a supporting matrix.

36. The apparatus of claim 20, wherein the background signal has a shorter lifetime that the probe.

37. The apparatus of claim 20, further comprising the step of imaging the fluorescence, phosphorescence, or delayed fluorescence from the sample.

38. The apparatus of claim 20, further comprising the step of imaging the fluorescence, phosphorescence, or delayed fluorescence from a virus, bacterial, fungi, plant, animal, or human.

39. The apparatus of claim 20, further comprising a microscope for imaging the fluorescence, phosphorescence, or delayed fluorescence from the sample.

40. The apparatus of claim 20, further comprising an apparatus for imaging the fluorescence, phosphorescence, or delayed fluorescence from a virus, bacterial, fungi, plant, animal, or human.

41. A kit for retrofitting an apparatus to produce one or more bursts of electromagnetic pulses, each of the bursts comprising two or more pulses comprising:
a burst generator that creates a burst of two or more electromagnetic radiation pulses from a source pulse by separating the source pulse into two or more pulses to form a burst of pulses, wherein the spacing between each burst of pulses, and the frequency of the pulses, is selected to match the excitation of one or more probes.

42. The kit of claim 41, wherein the burst generator comprises at least one of mirrors, prisms, gratings, splitters, optoelectronic elements, mechanical elements, optic fiber, or optic fiber loops.

43. The kit of claim 41, further comprising an attachment for a microscope to the one or more bursts of pulses in communication with a target.

44. The kit of claim 41, wherein the probe is selected from the group of long-lived emitters like ADOTA group of dyes, pyrene and dansyl type emitters, porphyrins based dyes, lanthanides probes, metal-ligand complex probes like ruthenium probes, quantum dots, or quantum nanomaterials, nanodiamonds; also probes 7-Amino-actinomycin D; Acridine orange; Acridine yellow; Alexa Fluor; AnaSpec; Auramine O; Auramine-rhodamine stain; Benzanthrone; 9,10-Bis(phenylethynyl)anthracene; 5,12-Bis(phenylethynyl)naphthacene; CFDA-SE; CF SE; Calcein; Carboxyfluorescein; 1-Chloro-9,10-bis(phenylethynyl)anthracene; 2-Chloro-9,10-bis(phenylethynyl)anthracene; Coumarin; Cyanine; DAPI; Dark quencher; Dioc6; DyLight Fluor; Ethidium bromide; Fluorescein; Fura-2; Fura-2-acetoxymethyl ester; Green fluorescent protein; Hilyte Fluor; Hoechst stain; Indian yellow; Luciferin; Perylene; Phycobilin; Phycoerythrin; Phycoerythrobilin; Propidium iodide; Pyranine; Rhodamine; RiboGreen; Rubrene; Ruthenium(II) tris(bathophenanthroline disulfonate); SYBR Green; Stilbene; TSQ; Texas Red; Umbelliferone; and Yellow fluorescent protein.

45. The kit of claim 41, wherein the burst generator generates one or more bursts of pulses that exposed the probe to 2, 3, 4, 5, 6, 7, 8, 9, 10, 11, 12, 13, 14, 15, 20, 25, 30, 35, 40, 45, 50, 100, 200, 300, 400, 500, 750, 1,000, $10^5$, $10^6$, $10^7$ or more burst trains before, during or prior to detection.

46. The kit of claim 41, wherein the burst generator generates one or more bursts that comprises 2, 3, 4, 5, 6, 7, 8, 9, 10, 11, 12, 13, 14, 15, 20, 25, 30, 35, 40, 45, 50, 100, 200, 300, 400, 500, 750, 1,000 pulses before, during or prior to detection.

47. The kit of claim 41, further comprising a light source capable of transmitting the source pulse.

* * * * *